(12) United States Patent
Caylor, III

(10) Patent No.: US 8,685,091 B2
(45) Date of Patent: Apr. 1, 2014

(54) SYSTEM, METHOD, AND DEVICE FOR MONITORING ORTHOPAEDIC IMPLANT DATA OVER A CELLULAR NETWORK

(75) Inventor: Edward J. Caylor, III, Fort Wayne, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1390 days.

(21) Appl. No.: 11/537,338

(22) Filed: Sep. 29, 2006

(65) Prior Publication Data

US 2008/0133009 A1 Jun. 5, 2008

(51) Int. Cl.
*A61F 2/28* (2006.01)

(52) U.S. Cl.
USPC .......................... 623/16.11; 623/914; 128/904

(58) Field of Classification Search
USPC .................. 623/20.33, 20.34; 600/302; 607/2
See application file for complete search history.

(56) References Cited

U.S. PATENT DOCUMENTS

| | | | |
|---|---|---|---|
| 5,252,102 A * | 10/1993 | Singer et al. ..................... 623/24 |
| 6,689,056 B1 * | 2/2004 | Kilcoyne et al. .............. 600/300 |
| 6,804,558 B2 | 10/2004 | Haller et al. |
| 2002/0024450 A1 * | 2/2002 | Townsend et al. ....... 340/870.16 |
| 2004/0113790 A1 | 6/2004 | Hamel et al. |
| 2005/0159787 A1 | 7/2005 | Linberg et al. |
| 2005/0288736 A1 | 12/2005 | Persen et al. |
| 2006/0173552 A1 | 8/2006 | Roy |
| 2006/0178583 A1 * | 8/2006 | Montegrande et al. ....... 600/486 |

FOREIGN PATENT DOCUMENTS

| | | |
|---|---|---|
| WO | 2006034273 | 3/2006 |
| WO | 2006055547 | 5/2006 |

OTHER PUBLICATIONS http://www.mlive.com/news/sanews/index.ssf?/base/news-19/1155734420198690.xml&coll=9, "In a first, heart that's in distress will e-mail the doctor for help", *The Saginaw News*, Jill Armentrout, Aug. 16, 2006.
European Search Report for European Application No. 07253853.1-2310, Feb. 1, 2008, 7 pgs.

\* cited by examiner

*Primary Examiner* — David Isabella
*Assistant Examiner* — Yashita Sharma
(74) *Attorney, Agent, or Firm* — Barnes & Thornburg LLP

(57) ABSTRACT

A system, method, and device for monitoring implant sensor data over a cellular network includes a portable computing device, a controller, and an orthopaedic prosthesis configured to communicate with the controller over the cellular network. The orthopaedic prosthesis includes one or more implant sensors configured to generate implant sensor data and a cellular transmitter or transceiver configured to transmit the implant sensor data to the controller over the cellular network. The controller or the orthopaedic prosthesis may initiate the cellular communication. The implant sensor data is transmitted to the portable computing device by the controller. The portable computing device is configured to display the implant sensor data, or indicia thereof, to a user. The portable computing device and controller may also be used to update one or more programs executed by the orthopaedic prosthesis.

8 Claims, 9 Drawing Sheets

SYSTEM, METHOD, AND DEVICE FOR MONITORING ORTHOPAEDIC IMPLANT DATA OVER A CELLULAR NETWORK

TECHNICAL FIELD

The present disclosure relates generally to systems and methods for transmitting, receiving, and/or monitoring orthopaedic implant sensor data.

BACKGROUND

Orthopaedic implants or prostheses are implanted into patients by orthopaedic surgeons to, for example, correct or otherwise alleviate bone and/or soft tissue loss, trauma damage, and/or deformation of the bone(s) of the patients. Some orthopaedic prostheses include one or more sensors for detecting or measuring various effects or forces acting on the orthopaedic prostheses and/or the surrounding environment. After initial implantation, it is often desirable to periodically monitor the implant sensor data particularly when the patient is experiencing problems with the orthopaedic prosthesis. However, even when the patient is experiencing an ongoing problem with an orthopaedic prosthesis, the patient must typically schedule an appointment for examination by the orthopaedic surgeon or other healthcare provider in their office or hospital. As such, there is often a delay between the time that the patient is first aware of the problem and the scheduled appointment. Such a delay may reduce the effectiveness of the medical analysis of the orthopaedic prosthesis. For example, the problem may be intermittent and may not be observable at the time of the appointment and/or may change over time. In addition, the patient may be experiencing discomfort during the delay making prompt medical analysis of the orthopaedic prosthesis desirable.

SUMMARY

According to one aspect, a medical device includes an orthopaedic prosthesis having a circuit secured thereto. The circuit may include a sensor, a cellular transmitter, and a processor. The sensor may be configured to generate implant sensor data and the cellular transmitter may be configured to transmit data over a cellular network. The processor may be electrically coupled to the sensor and/or the cellular transmitter. The processor may be configured to receive the implant sensor data from the sensor and transmit the implant sensor data over the cellular network using the cellular transmitter. The cellular transmitter may form a portion of a cellular transceiver in some embodiments. The cellular transceiver may be configured to receive data, such as programming data, over the cellular network. In such embodiments, the processor may be configured to transmit the implant sensor data in response to a signal received from a controller over the cellular network via the cellular transceiver. Additionally, wherein the data is embodied as programming data, the processor may be configured to update a program of the orthopaedic prosthesis using the programming data.

The orthopaedic prosthesis may also include a memory device. The memory device may have stored therein a first implant serial number associated with the orthopaedic prosthesis. In such embodiments, the processor may be configured to retrieve the first implant serial number from the memory device and compare the first implant serial number to a second implant serial number received over the cellular network via the cellular transceiver. Additionally, the processor may be configured to transmit the implant sensor data if the first implant serial number is equal to the second implant serial number. In some embodiments, the processor may be configured to store the implant sensor data in the memory device, retrieve the stored implant sensor data, and transmit the retrieved implant sensor data over the cellular network via the cellular transmitter.

Additionally, in some embodiments, the processor may be configured to compare the implant sensor data to a predetermined threshold value and initiate communication with the controller over the cellular network using the cellular transmitter based on such comparison. Once cellular communication is established, the processor may be configured to transmit the implant sensor data to the controller over the cellular network using the cellular transmitter. In addition, the processor may be configured to retrieve implant sensor data from the memory device and transmit the retrieved implant sensor data to the controller over the cellular network using the cellular transmitter once cellular communication is established. Further, in some embodiments, the processor may be configured to retrieve an implant serial number from the memory device and transmit the implant serial number to the controller over the cellular network using the cellular transmitter.

According to another aspect, a system for monitoring implant data over a cellular network may include a controller and an orthopaedic prosthesis. The orthopaedic prosthesis may include a cellular transceiver configured to communicate with the controller over the cellular network. The orthopaedic prosthesis may also include a sensor configured to generate implant sensor data. In such embodiments, the cellular transceiver of the orthopaedic prosthesis may be configured to transmit the implant sensor data to the controller over the cellular network. The system may also include portable computing device. The portable computing device may be embodied as, for example, a computer, a laptop computer, a personal digital assistant (PDA), a cellular phone, or the like. The portable computing device may be configured to communicate with the controller over a network such as a local area network (LAN), a wide area network, the Internet, a cellular network, and/or the like. The controller may be configured to transmit the implant sensor data to the portable computing device. In response, the portable computing device may be configured to display the implant sensor data, or indicia thereof, to a user of the portable computing device. In some embodiments, the portable computing device may be configured to transmit an implant serial number and a passcode to the controller over the network. The implant serial number and/or passcode may be supplied or entered by a user of the portable computing device.

The system may also include a database communicatively coupled to the controller. In such embodiments, the controller may be configured to verify an association or relation between the implant serial number and the passcode using data stored in the database. For example, the controller may be configured to verify that the user identified by the supplied passcode is authorized to communicate with the orthopaedic prosthesis identified by the implant serial number. Additionally, in some embodiments, the controller may be configured to retrieve contact data associated with the orthopaedic prosthesis from the database based on the implant serial number. The controller may be configured to subsequently initiate cellular communication with the orthopaedic prosthesis using the contact data. The controller may also be configured to transmit programming data to the orthopaedic prosthesis over the cellular network. In such embodiments, the orthopaedic prosthesis may be configured to update a program of a processor of the orthopaedic prosthesis using the programming data.

According to yet another aspect, a method of monitoring implant sensor data over a cellular network may include receiving the implant sensor data from an orthopaedic prosthesis over the cellular network. The method may also include receiving an implant serial number and a passcode from a portable computing device. In such embodiments, the method may further include verifying an association between the implant serial number and the passcode. The association between the implant serial number and the passcode may be verified by retrieving data from a database and comparing the data to the implant serial number and the passcode. The method may also include retrieving contact data associated with the orthopaedic prosthesis from a database based on the implant serial number and initiating cellular communication with the orthopaedic prosthesis using the contact data.

In some embodiments, the method may include retrieving implant sensor data from a memory device of the orthopaedic prosthesis. In such embodiments, the method may further include transmitting the retrieved implant sensor data over the cellular network. The method may also include receiving a first implant serial number over a cellular network and retrieving a second implant serial number from a memory device of the orthopaedic prosthesis. The method may additionally include comparing the first implant serial number and the second implant serial number and transmitting the implant sensor data over the cellular network based on such comparison. In some embodiments, the method may further include transmitting the implant sensor data to a portable computing device. In such embodiments, the implant sensor data, or indicia thereof, may be displayed on the portable computing device. Yet further, in some embodiments, the method may include receiving the implant sensor data from an implant sensor of the orthopaedic prosthesis, comparing the implant sensor data to a predetermined threshold, and transmitting the implant sensor data over the cellular network using a cellular transmitter of the orthopaedic prosthesis based on the comparing step. Additionally, the method may include transmitting programming data to the orthopaedic prosthesis over the cellular network and updating a program of the orthopaedic prosthesis using the programming data.

BRIEF DESCRIPTION OF THE DRAWINGS

The detailed description particularly refers to the following figures, in which.

DETAILED DESCRIPTION OF THE DRAWINGS

Figure 1:
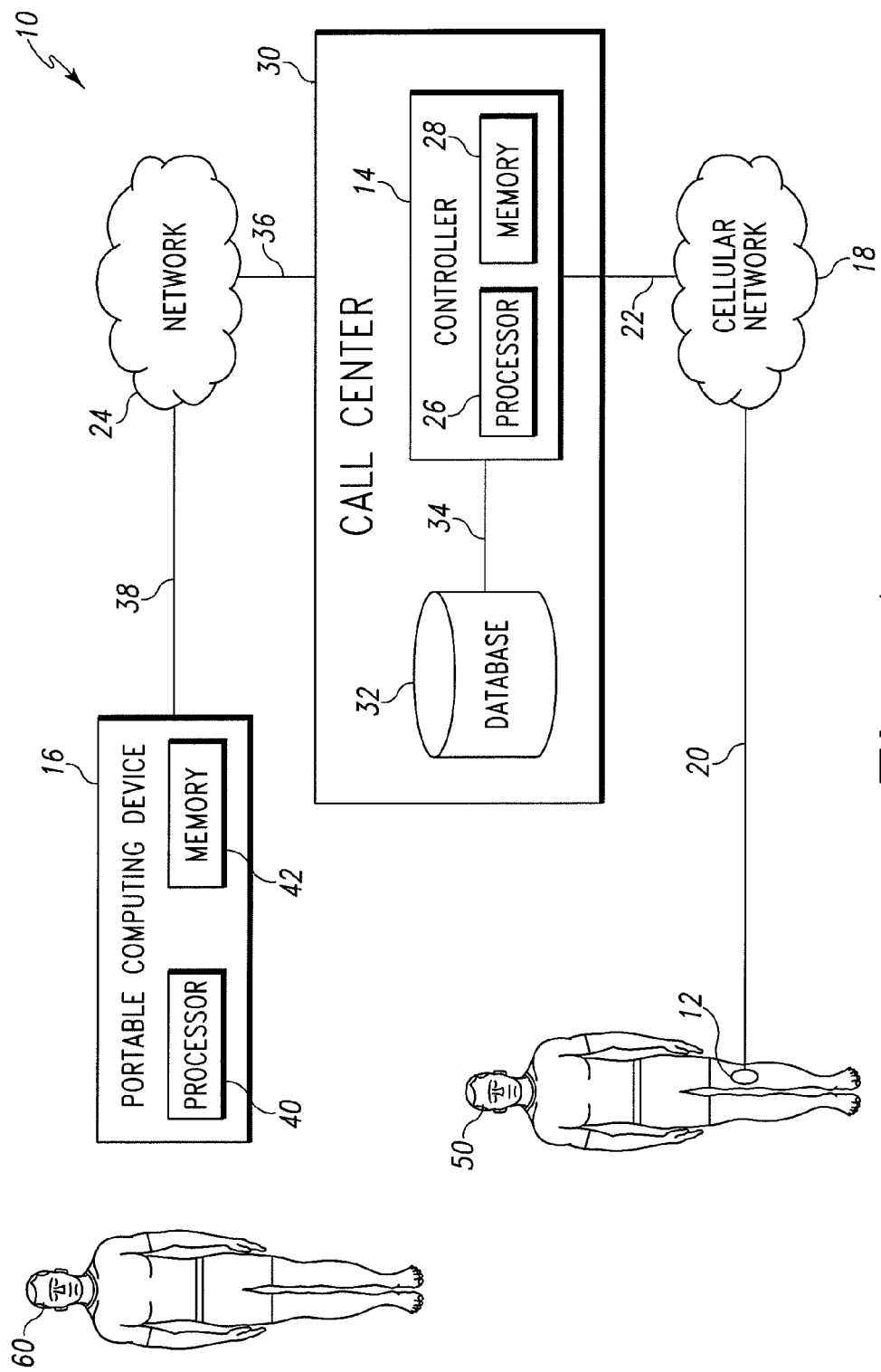
FIG. 1 is a simplified block diagram of a system for monitoring implant sensor data over a cellular network.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a system 10 for monitoring implant sensor data over a cellular network 18 includes an orthopaedic implant or prosthesis 12, a controller 14, and a portable computing device 16. The orthopaedic prosthesis 12 is configured to communicate with the controller 14 over the cellular network 18. The orthopaedic prosthesis 12 may be embodied as any type of orthopaedic prosthesis such as, for example, a knee implant, a hip implant, a shoulder implant, or the like configured to be implanted in a patient 50. As discussed below in regard to FIG. 2, the orthopaedic prosthesis 12 includes a number of electrical devices such as a cellular transmitter/transceiver and one or more implant sensors. The orthopaedic prosthesis 12 is communicatively coupled to the cellular network 18 via a wireless cellular communication link 20. In some embodiments, the communication link 20 is established only while cellular communication between the orthopaedic prosthesis 12 and the controller 14 is desired. As used herein, the term "cellular communication" is intended to refer to any transmission or reception of data over a cellular network.

The cellular network 18 may be embodied as any type of cellular wireless network and may include any number of devices configured to facilitate cellular communication between the orthopaedic prosthesis 12 and the controller 14. For example, the cellular network 18 may include one or more cellular carrier networks electrically coupled to any number of carrier towers having any number of cellular antennas coupled thereto. The cellular carrier network(s) may include such elements as Mobile Telephone or Telecommunications Switch Offices (hereinafter sometimes MTSO), carrier base stations, interconnections operable to couple the various elements of the cellular carrier network, additional towers, antennas, and other communication devices useful in propagating data across the cellular network 18. Additionally, in some embodiments, the cellular network 18 may include portions of the local Public Switch Telephone Network (hereinafter sometimes PSTN).

The cellular network 18 may use any cellular transmission protocol to facility the cellular communication between the orthopaedic prosthesis 12 and the controller 16. For example, in some embodiments, the cellular network 18, or portion thereof, is embodied as an analog wireless network such as an Advanced Mobile Phone Service (hereinafter sometimes AMPS) network, a Narrowband Advanced Mobile Phone Service (hereinafter sometimes NAMPS) network, or other analog wireless network. In such embodiments, the orthopaedic prosthesis 12 and the controller 14 are configured to communicate with each other over the cellular network 18 using an analog wireless transmission protocol or technology such as, for example, a Frequency Division Multiple Access (hereinafter sometimes FDMA) transmission protocol.

In other embodiments, the cellular network 18, or portion thereof, may be embodied as a digital wireless network such as a Global System for Mobile Communications (hereinafter sometimes GSM) network, a Personal Communications Systems (hereinafter sometimes PCS) network, a Digital Advanced Mobile Phone Service (hereinafter sometimes DAMPS) network, or other digital wireless network which, in some implementations, may use, communicate with, or rely on portions of an analog wireless network such as an AMPS network. In the case of a digital network, the cellular network 18 may be embodied as a circuit switched digital wireless network, a packet switched wireless network, or other type of digital wireless network including proprietary digital networks such as the Integrated Digital Enhanced Network (hereinafter sometimes iDEN). In embodiments wherein the cellular network 18 is embodied as or includes such digital wireless networks, the orthopaedic prosthesis 12 and the controller 14 are configured to communicate with each other over the cellular network 18 using a digital wireless transmission protocol or technology such as, for example, a Time Division Multiple Access (hereinafter sometimes TDMA) transmission protocol, a Code Division Multiple Access (hereinafter sometimes CDMA) transmission protocol, a Code Division Multiple Access 2000 (hereinafter sometimes CDMA2000) transmission protocol, a Wideband Code Division Multiple Access (hereinafter sometimes WCDMA) transmission protocol, and/or a Time Division-Synchronous Code Division Multiple Access (hereinafter sometimes TD-SCDMA) transmission protocol.

The controller 14 is coupled to the cellular network 18 via a communication link 22. The communication link 22 may be embodied as any type and number of communication links capable of facilitating communication between the controller 14 and the cellular network 18. The communication link 22 may be embodied as a wired communication link, a wireless communication link, or a combination thereof. For example, the communication link 22 may be embodied as or otherwise include any number of wires, cables, printed circuit board traces, vias, and/or the like.

The controller 14 includes a processor 26 and a memory device 28. The processor 26 may be embodied as any type of processor including, for example, discrete circuitry (e.g., a collection of logic devices), general purpose integrated circuit(s), and/or application specific integrated circuit(s) (i.e., ASICs). The memory device 28 may be embodied as any type of memory device and may include one or more memory types, such as, random access memory (i.e., RAM) and/or read-only memory (i.e., ROM). In addition, the controller 14 may include other devices and circuitry typically found in a computer for performing the functions described herein such as, for example, a hard drive, input/output circuitry, and the like.

The controller 14 forms a portion of a call center 30. The call center 30 may include any number of controllers 14 configured to communicate with the portable computing device 16 and the orthopaedic prosthesis 12. In some embodiments, the call center 30 may form a portion of a hospital network. The call center 30 includes a database 32, which may be embodied as any type of database capable of storing orthopaedic prosthesis-related data. Although illustrated in FIG. 1 as a single database, it should be appreciated that the database 32 may be embodied as any number of separate databases, file folders, flat files, or other storage locations.

The orthopaedic prosthesis-related data may include, for example, orthopaedic prosthesis serial numbers, passcodes assigned to individual surgeons, cellular telephone numbers and other contact data, implant sensor data, and/or the like. The orthopaedic prosthesis-related data may be stored in the database 32 in association with, indexed by, or otherwise retrievable based on each data type. For example, in one particular embodiment, implant serial numbers are stored in association with passcodes assigned to the orthopaedic surgeons or other healthcare providers authorized to monitor the orthopaedic prosthesis identified by the particular implant serial number as discussed in more detail below. The patient database 32 may be located at the same location as the controller 14 (e.g., within the same hospital) or may be located remotely therefrom.

The controller 14 is communicatively coupled to the database 32 via a number of communication links 34. The communication links 34 may be embodied as any type of communications links such as a wired communication link, a wireless communication link, or a combination thereof. For example, the communication link 34 may be embodied as or otherwise include any number of wires, cables, printed circuit board traces, vias, and/or the like.

The controller 14 is also configured to communicate with the portable computing device 16 via a network 24. The network 24 may be embodied as any type of network capable of facilitating communication between the portable computing device 16 and the controller 14. For example, the network 24 may be embodied as or include a local area network (LAN), a wide area network (WAN), or may form a portion of a publicly-accessible, global network such as the Internet. In addition, the network 24 may be embodied as a wired network, a wireless network, or a combination thereof.

The controller 14 is coupled to the network 24 via a communication link 36. The controller 14 is also coupled to the cellular network 18 via a communication link 22. The communication links 22, 36 may be embodied as any type of communication links capable of facilitating communication between the controller 14 and the cellular network 18 and the network 24, respectively. As such, the communication links 22, 36 may be embodied as any type of communications links such as wired communication links, a wireless communication links, or a combination thereof. For example, the communication link 22, 36 may be embodied as or otherwise include any number of wires, cables, printed circuit board traces, vias, and/or the like.

The portable computing device 16 is configured to communicate with the controller 14 over the network 24. The portable computing device 16 is also communicatively coupled to the network 24 via a number of communication links 38. Similar to the communication links 22, 36, the communication links 38 may be embodied as any type of communications links such as a wired communication link, a wireless communication link, or a combination thereof. For example, the communication link 38 may be embodied as or otherwise include any number of wires, cables, printed circuit board traces, vias, and/or the like.

The portable computing device 16 may be embodied as any type of computing device usable by an orthopaedic surgeon or other orthopaedic healthcare provider 60 to transmit data to and receive data from the controller 14 over the network 24. For example, the portable computing device 16 may be embodied as a Personal Digital Assistant (hereinafter sometimes PDA), a laptop or desktop computer, a PDA mobile phone, and/or similar computing devices suitable for communicating with the controller 14 over the network 24 and displaying data to the orthopaedic healthcare provider 60.

The illustrative portable computing device 16 includes a processor 40 and a memory device 42. The processor 40 may be embodied as any type of processor including, for example, discrete circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the portable computing device 16 may include other devices and circuitry typically found in a computer for performing the functions described herein such as, for example, a hard drive, input/output circuitry, and the like. For example, the portable computing device 16 may include a transmitter/receiver, network card, modem, and/or the like for communicating with the controller 14 over the network 24.

In use, the orthopaedic healthcare provider 60 may operate the portable computing device 16 to monitor implant sensor data generated by the orthopaedic prosthesis 12 and/or update programming of the orthopaedic prosthesis 12 as described in more detail below in regard to FIGS. 3-5. To do so, the orthopaedic healthcare provider may enter an implant serial number and a passcode into the portable computing device 16, which is subsequently transmitted to the controller 14 via the network 24. The implant serial number may be embodied as any type of data that uniquely identifies the orthopaedic prosthesis 12 from other orthopaedic prostheses used in the system 10. As such, the implant serial number may include any number and type of characters including numeric characters and alphabetic characters. In one particular embodiment, the implant serial number is identical to, based on, or otherwise derived from a cellular telephone or access number associated with the orthopaedic prosthesis device 12. Similarly, the passcode may be embodied as any type of data that identifies the orthopaedic healthcare provider 60. The passcode may be unique to the orthopaedic healthcare provider 60 or to some other entity such as a hospital, a group of orthopaedic healthcare providers, or the like.

Once the controller 14 receives the implant serial number and passcode from the portable computing device 16, the controller 14 verifies that the orthopaedic surgeon or healthcare provider associated with the passcode is authorized to communicate with the orthopaedic prosthesis 12 identified by the implant serial number. To do so, the controller 14 may retrieve data, such as a look-up table, from the database 32 and compare the passcode and implant serial number to the retrieved data. If the user identified by the passcode is authorized to communicate with the orthopaedic prosthesis sensor, the controller 14 initiates cellular communication with the orthopaedic prosthesis 12 and receives implant sensor data transmitted from the orthopaedic prosthesis 12 over the cellular network 18.

The controller 14 subsequently transmits the implant sensor data to the portable computing device 16 via the network 24. The implant sensor data, or indicia thereof such as a graph, chart, or the like, is displayed to the orthopaedic healthcare provider 60 via a display device or the like of the portable computing device 16. In addition, the orthopaedic healthcare provider 60 may operate the portable computing device 16 to supply programming data to the orthopaedic prosthesis 12 via the cellular network 18. The programming data is used by the orthopaedic prosthesis 12 to update a program executed by electronic circuitry of the orthopaedic prosthesis 12. Additionally or alternatively, in some embodiments as discussed in more detail below in regard to FIGS. 6-8, the orthopaedic prosthesis 12 may be configured to initiate cellular communication with the controller 14 based on a predetermined condition such as the value(s) of the implant sensor data.

Figure 2:
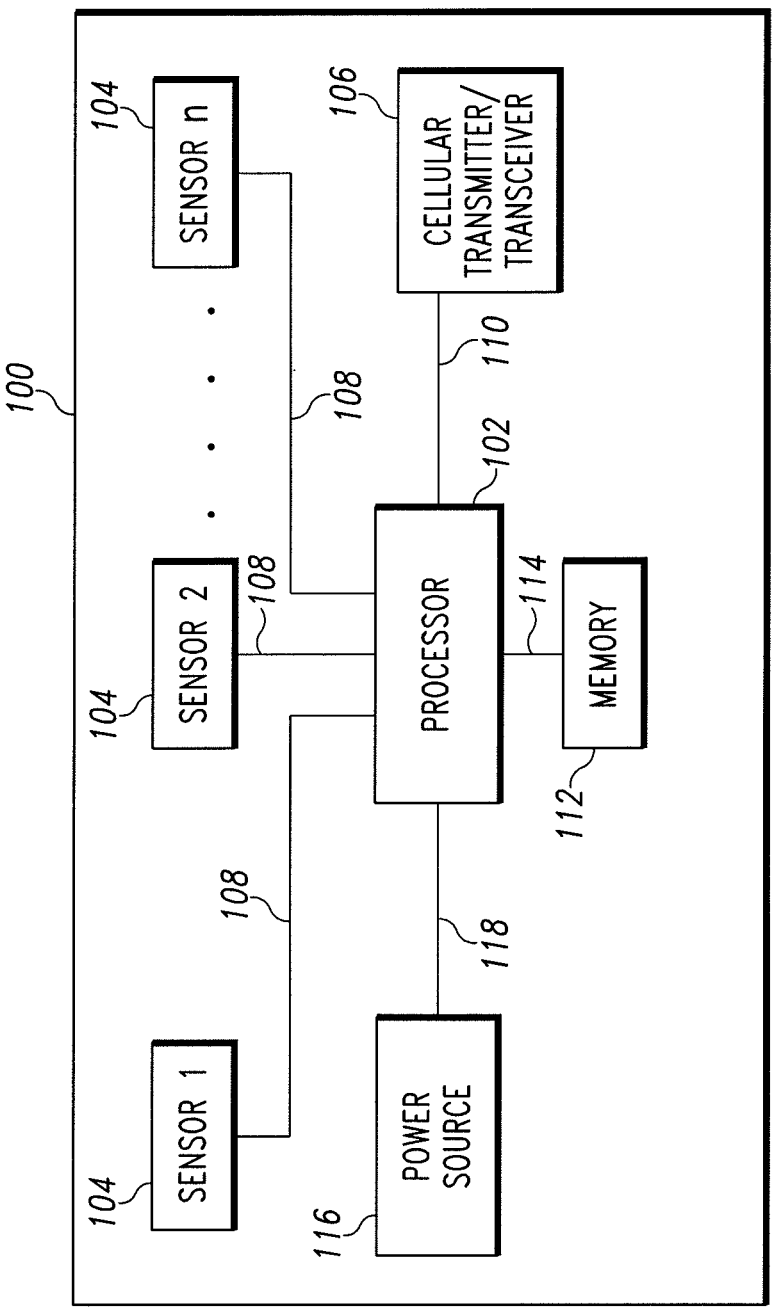
FIG. 2 is a simplified block diagram of one embodiment of an orthopaedic prosthesis of the system of FIG. 1.

Referring now to FIG. 2, the orthopaedic prosthesis 12 includes electronic circuitry 100 coupled to or otherwise housed therein. The electronic circuitry 100 includes a processor 102, one or more implant sensors 104, and a cellular transmitter and/or receiver (e.g., a cellular transceiver) 106. The processor 102 is coupled to the sensor(s) 104 via a number of communication links 108 and to the cellular transmitter/transceiver 106 via a number of communication links 110. The communication links 108, 110 may be embodied as or otherwise include any number of wires, cables, printed circuit board traces, vias, and/or the like.

The processor 102 may be embodied as any type of processor capable of receiving implant sensor data from the implant sensor(s) 104 and transmitting the implant sensor data over the cellular network 18 using the cellular transmitter/transceiver 106. For example, the processor 102 may be embodied as, or otherwise include discrete processing circuits (e.g., a collection of logic devices), general purpose integrated circuit(s), and/or application specific integrated circuit(s) (i.e., ASICs).

The electronic circuitry 100 may include any number of implant sensors 104. The implant sensor(s) 104 may be embodied as any type of implant sensor configured to generate implant sensor data of a parameter of interest. For example, the implant sensor(s) 104 may be embodied as a pressure sensor, a load sensor, a temperature sensor, a hall-effect sensor, or the like. The implant sensor data is transmitted to the processor 102 via the communication links 108.

As discussed above, the cellular transmitter 106 may be embodied as any transmitter or transceiver configured to transmit and/or receive data over the cellular network 18. That is, the cellular transmitter 106 is configured to transmit and/or receive data using a wireless carrier frequency and communication protocol/technology supported or otherwise used by the cellular network 18. As such, the cellular transmitter 106 may include any number of circuits and electronic devices (e.g., a cellular antenna) and, in some embodiments, may be similar to the cellular transmitters/transceivers used in typical cellular telephones and other cellular communication devices.

The electronic circuitry 100 also includes a memory device 112. The memory device 112 is communicatively coupled to the processor 102 via a number of communication links 114. Similar to communication links 108, 110, the communication links 114 may be embodied as or otherwise include any number of wires, cables, printed circuit board traces, vias, and/or the like. The memory device 12 may be embodied as any type of memory device capable of storing implant sensor data and, in some embodiments, programming or software code. The memory device 12 may include one or more memory types, such as, random access memory (i.e., RAM) and/or read-only memory (i.e., ROM).

The processor 102 and other devices of the electronic circuitry 100 receive power from a power source 116. The power source 116 may be embodied as any type of power source capable of supplying power to the other devices of the electronic circuitry 100 sufficient to perform the functions described herein. The power source 116 may be a rechargeable power source or may be a permanent, continuous power source. For example, the power source 116 may be embodied as an implant battery, an inductively charged battery, a radio frequency (RF) charged battery, a vibration charged power source, a piezoelectric power source, a thin-film, battery, a thermal power source, an acoustic power source, and/or the like.

In use, the processor 102 may be configured to receive implant sensor data from the implant sensor(s) 104 and transmit the implant sensor data to the controller 14 over the cellular network 18 in response to a signal received from the controller 14. Additionally or alternatively, the processor 102 may be configured to store the implant sensor data in the memory device 112 and subsequently retrieve the stored implant sensor data for transmission to the controller 14 via the cellular network 18. Additionally, in some embodiments, the processor 102 is configured to execute a program stored in or otherwise defined by data stored in the memory device 112. The program or data may be embodied as software/firmware code executed by the processor and/or other data such as variable data used by a program executed by the processor 102. In such embodiments, the processor 102 may be configured to update the program stored in the memory device 112 with, based on, or using programming data received from the controller 106 via the cellular network 18.

Figure 3:
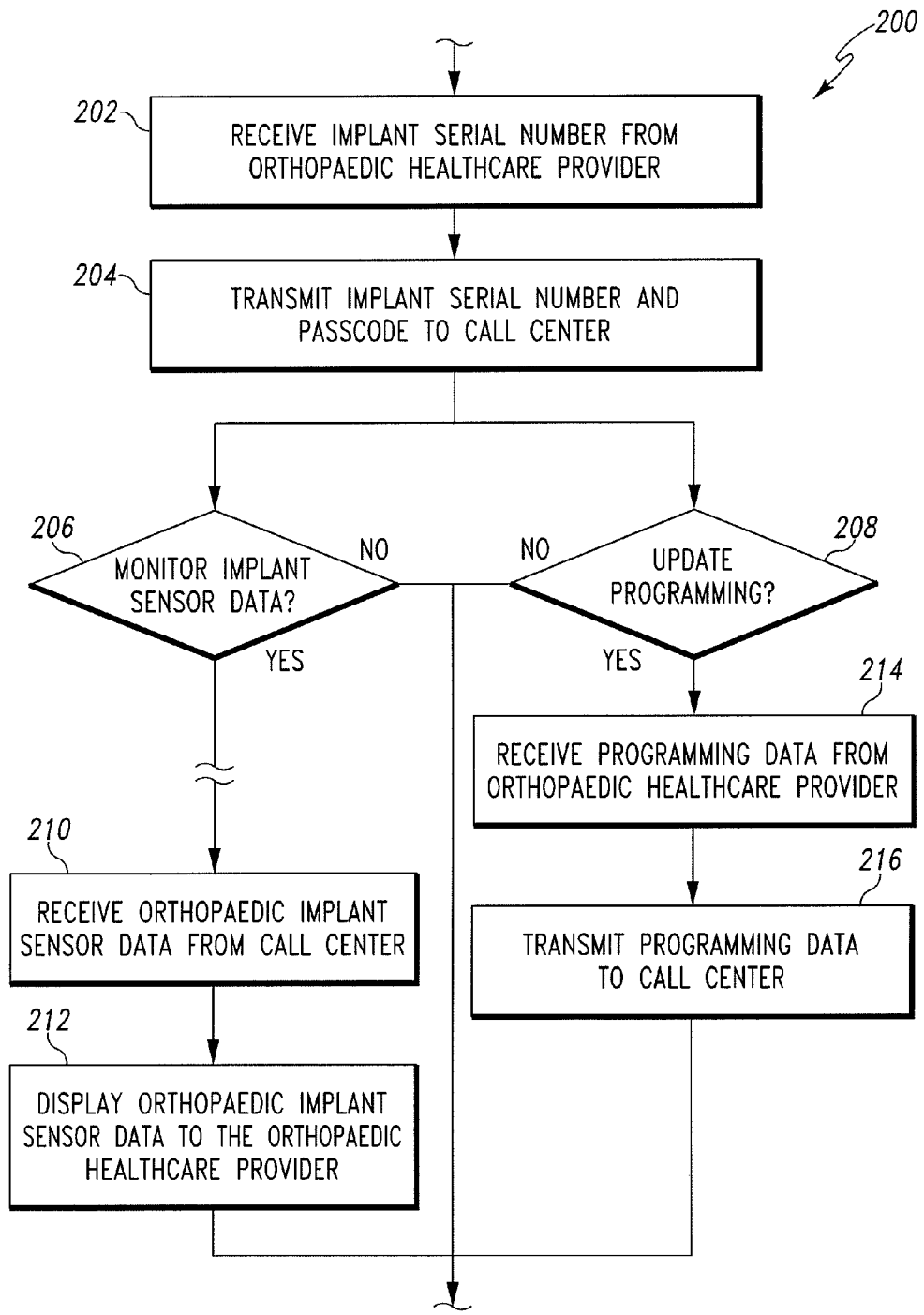
FIG. 3 is a simplified flowchart of one embodiment of an algorithm for monitoring orthopaedic prosthesis data over a cellular network that may be executed by a portable computing device of the system of FIG. 1.

In operation, the portable computing device 16 (i.e., the processor 40) of the system 10 may execute an algorithm 200 for monitoring orthopaedic prosthesis data as illustrated in FIG. 3. The algorithm 200 begins with a process step 202 in which the orthopaedic healthcare provider 60 (e.g., an orthopaedic surgeon) supplies the implant serial number associated with the orthopaedic prosthesis 12 of interest and the passcode associated with the orthopaedic healthcare provider 60. As discussed above in regard to FIG. 1, the implant serial number may be embodied as any type of data that uniquely identifies the orthopaedic prosthesis 12 from other orthopaedic prostheses and the passcode may be embodied as any type of data that identifies the orthopaedic healthcare provider 60.

The surgeon may supply the implant serial number and passcode via manually typing in the data or otherwise operating the portable computing device 16 such that the implant serial number and passcode are transmitted to the controller 14. In one particular embodiment, the orthopaedic healthcare provider 60 is prompted for the implant serial number and passcode (e.g., via a data field) once the orthopaedic healthcare provider 60 has initiated communication with the controller 14 over the network 24. Once the user has entered or otherwise supplied the implant serial number and passcode via the portable computing device 16, the implant serial number and passcode are transmitted from the portable computing device 16 to the controller 14 via the network 24 and communication links 36, 38 in process step 204.

Subsequently, the processor 40 of the portable computing device 16 determines if the orthopaedic healthcare provider 60 desires to monitor implant sensor data and/or update the programming of the orthopaedic prosthesis 12 in process steps 206, 208, respectively. To do so, the orthopaedic healthcare provider 60 may be prompted to choose which function the orthopaedic healthcare provider 60 would like to perform. Alternatively, both functions may be accessible by the orthopaedic healthcare provider 60 at any time. As such, it should be appreciated that the process steps 206, 208 may be executed in a sequential order or contemporaneously with each other.

If the processor 40 determines that the orthopaedic healthcare provider 60 desires to monitor implant sensor data in process step 206, the algorithm 200 advances to process step 210. In process step 210, the portable computing device 16 receives implant sensor data from the orthopaedic prosthesis 12 via the cellular network 18, the controller 14, and the network 24. The implant sensor data may be current implant sensor data and/or historical implant sensor data generated over a period of time. Subsequently, in process step 212, the received implant sensor data or indicia thereof is displayed to the orthopaedic healthcare provider 60 on a display screen, monitor, or other display device of the portable computing device 16. For example, the implant sensor data may be displayed in numerical form, in a graph, in a chart, or the like. As such, the orthopaedic healthcare provider 60 may monitor any parameter of interest that is measured by one or more of the implant sensors 104 in near-real time and/or monitor historic implant sensor data generated therefrom.

Referring back to process step 208, if the processor 40 determines that the orthopaedic healthcare provider 60 desires to update the programming of the orthopaedic prosthesis 12, programming data is received from the orthopaedic healthcare provider 60 in process step 214. The orthopaedic healthcare provider 60 may supply the programming data by manually typing in the data into the portable computing device 16 and/or by supplying the data on a readable media such as a diskette, a compact disc read only memory (CD ROM) media, digital video disk (DVD) media, universal serial bus (USB) flashdrive, or the like. In such embodiments, the portable computing device 16 includes a suitable media player such as a "floppy" disk drive, a CD ROM drive, a DVD drive, or the like.

The programming data may be embodied as any type of programming data usable by the electronic circuitry 100 of the orthopaedic prosthesis 12. For example, the programming data may be embodied as software/firmware code that is configured to be executed by the processor 102 of the orthopaedic prosthesis 12. Additionally, or alternatively, the programming data may be embodied as variable data configured to be used by a program executed by the processor 102. In addition, the programming data may be used by the electronic circuitry 100 to alter, change, or affect any function of the electronic circuitry 100. For example, the program data may alter the sampling rate used by the processor 102 to sample the implant sensor data generated by the implant sensor(s) 104, to alter threshold values or tolerance ranges, to alter communication protocols used by the cellular transmitter/transceiver 106, and/or any other device or function of the electronic circuitry 100.

Once the orthopaedic healthcare provider 60 has provided the programming data in process step 214, the programming data is transmitted to the controller 14 in process step 216. The programming data is transmitted to the controller 14 via the communication links 36, 38 and the network 24.

Figure 4A:
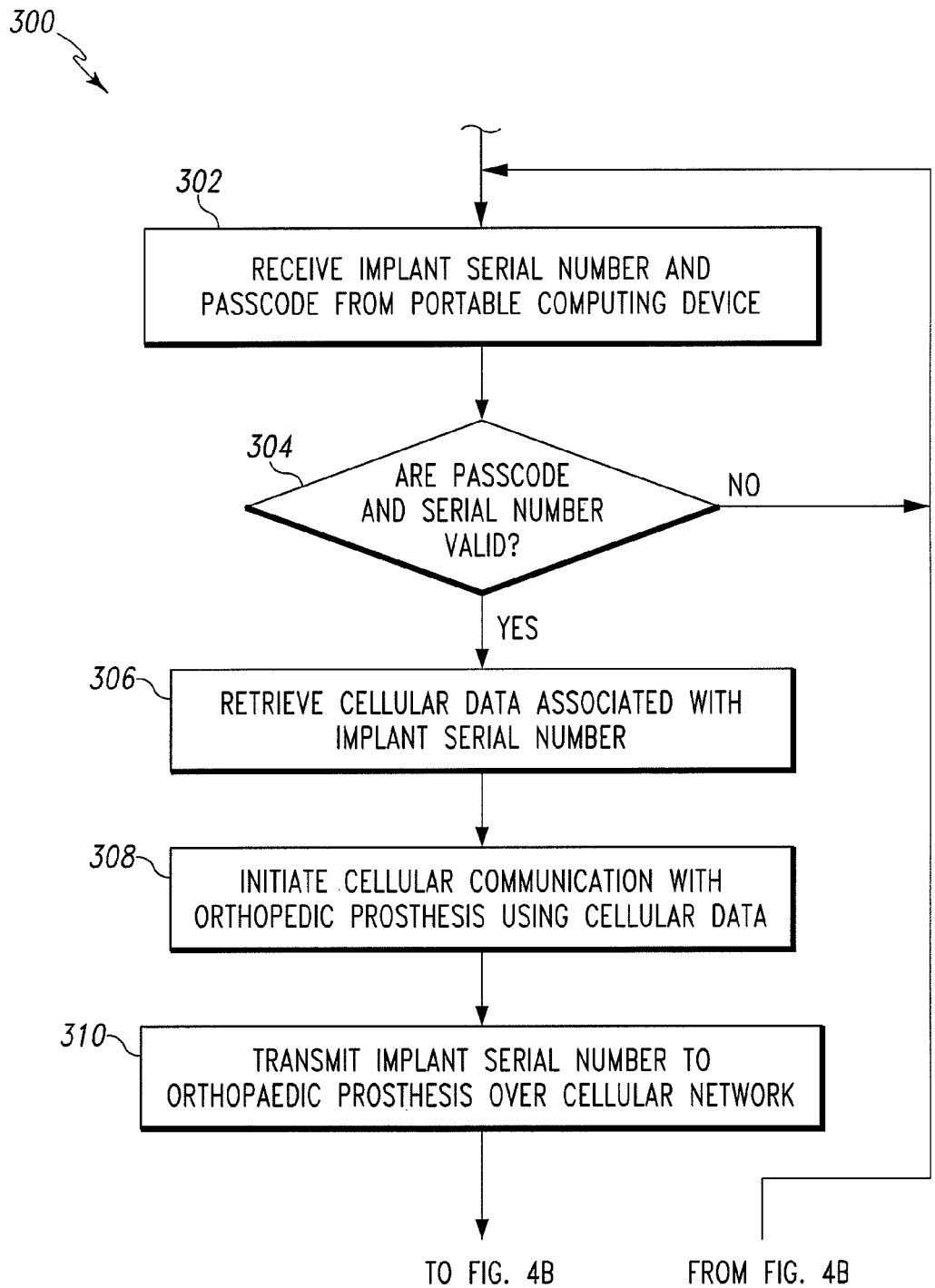
FIG. 4 is a simplified flowchart of one embodiment of an algorithm for communicating with an orthopaedic prosthesis over a cellular network that may be executed by a controller of the system of FIG. 1.
Figure 4B:
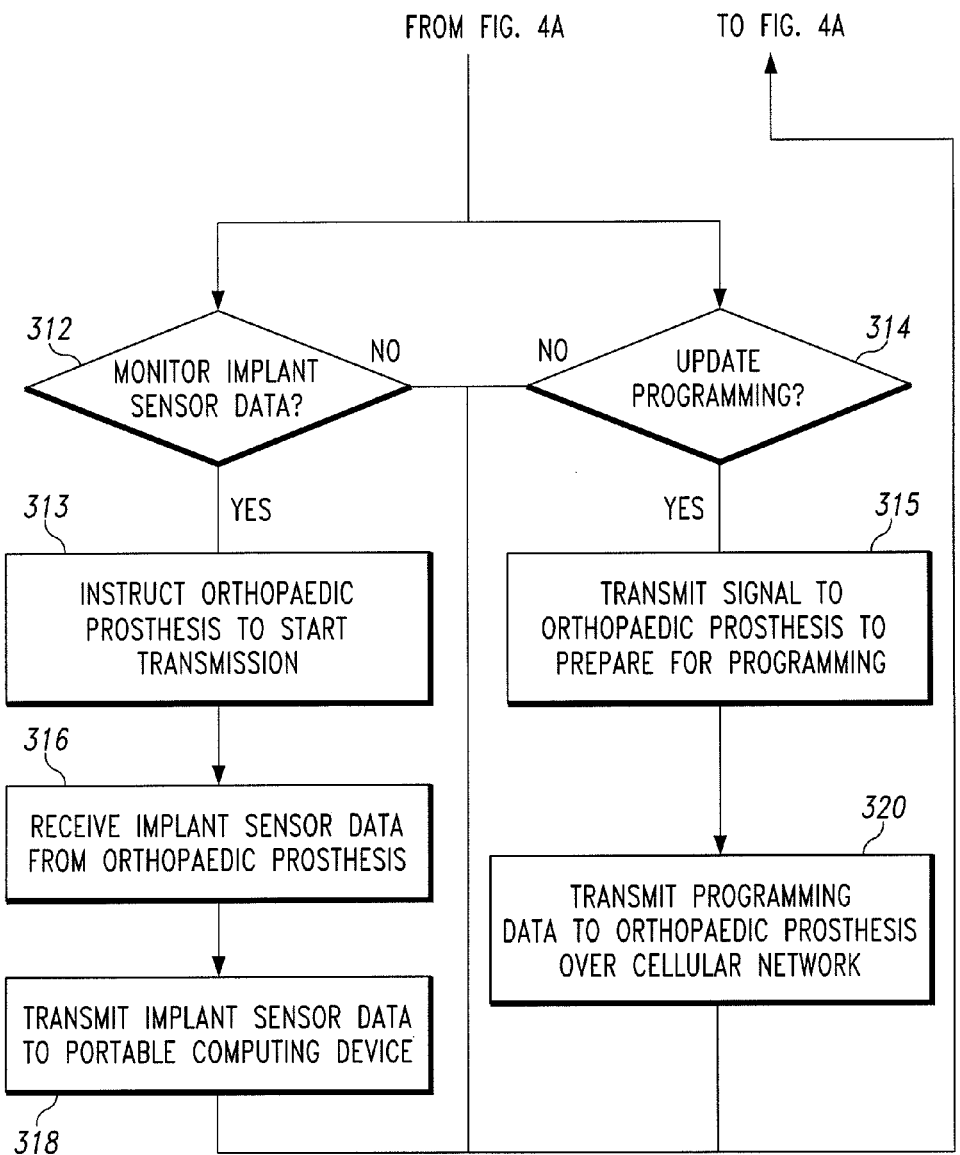

Referring now to FIG. 4, the controller 14 of the call center 30 is configured to execute an algorithm 300 for communicating with an orthopaedic prosthesis 12 over the cellular network 18 during the operation of the system 10. The algorithm 300 beings with a process step 302 in which the implant serial number and the passcode are received from the portable computing device 16 via the network 24. Next, in process step 304, the controller 14 determines if the implant serial number and passcode are valid. To do so, the controller 14 may retrieve data from the database and compare the retrieved data to the implant serial number and/or the passcode. Such a comparison may include any number of comparison steps. For example, the controller 14 may compare the received implant serial number to a list of implant serial numbers to verify that the received implant serial number is a valid implant serial number. Additionally, the controller 14 may compare the received passcode to a list of passcodes to verify that the received passcode is a valid passcode. Yet further, the controller 14 may retrieve a "look-up" table or the like, which relates passcodes to authorized implant serial numbers, from the database 32. If so, the controller 14 may compare the received implant serial number and passcode to the "look-up" table to verify that the orthopaedic healthcare provider identified by the received passcode is authorized to communicate with the orthopaedic prosthesis identified by the received implant serial number. Additionally, the controller 14 may use other algorithms and security measures to ensure the identity of the orthopaedic healthcare provider 60 and appropriate authorization.

If the implant serial number and/or passcode are not valid, the algorithm 300 loops back to process step 302 wherein the controller 14 waits to receive a new implant serial number and/or passcode. However, if the controller 14 determines that the implant serial number and passcode are valid in process step 304, the algorithm 300 advances to process step 306 in which the controller 14 retrieves contact data associated with the orthopaedic prosthesis 12 identified by the implant serial number from the database 32. The contact data may be embodied as any type of data with which the controller 14 may initiate cellular communication with the orthopaedic prosthesis 12. For example, in one embodiment, the contact data may be embodied as or may be based on a cellular telephone number or cellular access number of the orthopaedic prosthesis 12. The controller 14 may retrieve the contact data by, for example, retrieving a "look-up" table from the database 32 that indexes implant serial numbers to associated contact data. The controller 14 may then determine the appropriate contact data based on the received implant serial number. Alternatively, in some embodiments the implant serial number is embodied as the contact data. For example, the implant serial number may be embodied as the cellular telephone or access number of the orthopaedic prosthesis 12. In such embodiments, the process step 306 may be skipped.

Once the controller 14 has retrieved the contact data for the appropriate orthopaedic prosthesis 12 from the database 32, the controller 14 initiates cellular communication with the orthopaedic prosthesis 12 in process step 308. To do so, the controller 14 is configured to establish a cellular connection with the orthopaedic prosthesis 12 (via the cellular transmitter/transceiver 106) over the cellular network 18 using the contact data. For example, the controller 14 may transmit the appropriate data to the cellular network 18 to facilitate the cellular connection. In addition, the controller 14 and the orthopaedic prosthesis 12 may perform any number of initialization steps, "handshaking" steps, or the like to initialize or otherwise establish the cellular communication therebetween.

Once the controller 14 has initiated cellular communication with the orthopaedic prosthesis 12, the controller 14 is configured to transmit the received implant serial number to the orthopaedic prosthesis 12. To do so, the controller 14 transmits the received implant serial number over the cellular network 18 via the communication links 20, 22. Subsequently, the controller 14 determines if the orthopaedic healthcare provider 60 desires to monitor implant sensor data and/or update the programming of the orthopaedic prosthesis 12 in process steps 312, 314, respectively.

The controller 14 may determine if the orthopaedic healthcare provider 60 desires to monitor implant sensor data and/or update the programming of the orthopaedic prosthesis 12 based on, for example, data or signals received from the portable computing device 16 and/or from the orthopaedic prosthesis 12. For example, the controller 14 may determine that the orthopaedic healthcare provider 60 desires to monitor implant sensor data if implant sensor data is received from the orthopaedic prosthesis 12. Alternatively, the controller 14 may determine that the orthopaedic healthcare provider 60 desires to update the programming of the orthopaedic prosthesis if programming data is received form the portable computing device 16. Additionally or alternatively, the portable computing device 16 may be configured to transmit a signal or data to the controller 14 to inform the controller 14 that the orthopaedic healthcare provider 60 desires to monitor implant sensor data and/or update the programming of the orthopaedic prosthesis 12. As such, the controller 14 may use any one or more of a number of methods to determine which one or more functions to perform.

If the controller 14 determines that the orthopaedic healthcare provider 60 desires to monitor the implant sensor data in process step 312, the algorithm 300 advances to process step 313 in which the controller 14 transmits a signal to the orthopaedic prosthesis 12 instructing the prosthesis to begin transmitting the implant sensor data. Subsequently, in process step 316, the controller 14 receives implant sensor data from the orthopaedic prosthesis 12 via the cellular network 18. In response to receipt of the implant sensor data, the controller 14 is configured to transmit the implant sensor data to the portable computing device 16 via the network 24.

Referring back to process step 314, if the controller 14 determines that the orthopaedic healthcare provider 60 desires to update the programming of the orthopaedic prosthesis 12 in process step 314, the algorithm advances to process step 315 in which the controller 14 transmits a signal to the orthopaedic prosthesis 12 to prepare for a programming update. Subsequently, in process step 320, the controller 14 transmits the programming data to the orthopaedic prosthesis 12. To do so, the controller 14 transmits the programming data over the cellular network 18 via the communication links 20, 22. Once the controller 14 has transmitted the implant sensor data to the portable computing device 16 and/or transmitted the programming data to the orthopaedic prosthesis 12, the algorithm 300 loops back to process step 302 wherein the controller 14 waits to receive a new implant serial number and/or passcode.

Figure 5:
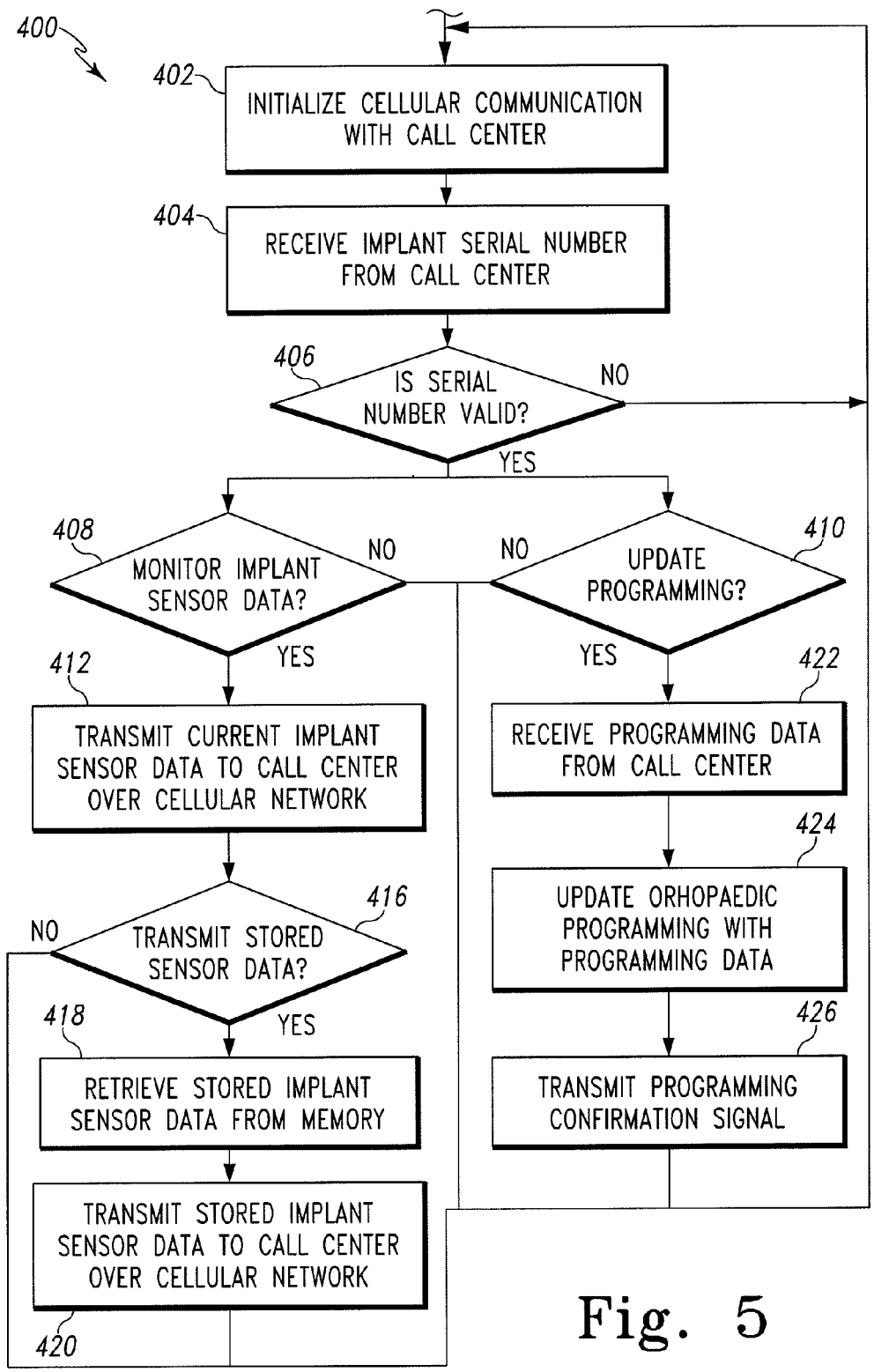
FIG. 5 is a simplified flowchart of one embodiment of an algorithm for communicating with a controller over a cellular network that may be executed by an orthopaedic prosthesis of the system of FIG. 1.

Referring now to FIG. 5, the orthopaedic prosthesis 12 of the system 10 is configured to execute an algorithm 400 for communicating with the controller 14 over the cellular network 18. The algorithm 400 begins with a process step 402 in which the orthopaedic prosthesis 12 initializes cellular communication with the controller 14 of the call center 30. As discussed above in regard to process step 308 of algorithm 300, the controller 14 is configured to initiate cellular communication with the orthopaedic prosthesis 12 in the illustrative embodiment. As such, in process step 402, the orthopaedic prosthesis 12 (i.e., the electronic circuitry 100) may be configured to perform any number of initialization steps, "handshaking" steps, or the like to initialize or otherwise establish the cellular communication with the controller 14 in process step 402.

Once the cellular communication with the controller 14 has been initialized or otherwise established in process step 402, the orthopaedic prosthesis 12 receives the implant serial number from the controller 14 in process step 404. In process step 406, the processor 102 is configured to determine if the received implant serial number is valid. To do so, in one embodiment, the processor 102 is configured to retrieve an implant serial number associated with the implant 12 from the memory device 112. The processor 102 compares the retrieved implant serial number with the implant serial number received from the controller 14 to determine if the implant serial numbers are equal or otherwise match within some predetermined amount of tolerance. In this way, the processor 102 ensures that the controller 14 has initiated cellular communication with the correct orthopaedic prosthesis 12. If the processor 102 determines that the received implant serial number is not valid, the algorithm 400 loops back to process step 402 wherein the electronic circuitry 100 of the orthopaedic prosthesis 12 waits for the initiation of a new cellular communication from the controller 14.

If, however, the processor 102 determines that the received implant serial number is valid in process step 406, the algorithm 400 advances to process steps 408 and 410. In process steps 408 and 410, the processor 102 determines if the orthopaedic healthcare provider 60 desires to monitor implant sensor data and/or update the programming of the electronic circuitry 100, respectively. The processor 102 may determine if the orthopaedic healthcare provider 60 desires to monitor implant sensor data and/or update the programming of the orthopaedic prosthesis 12 based on, for example, data or signals received from the controller 14. For example, the processor 102 may determine that the orthopaedic healthcare provider 60 desires to update the programming of the orthopaedic prosthesis 12 if programming data is received from the controller 14. Additionally or alternatively, the controller 14 may be configured to transmit a signal or data to the orthopaedic prosthesis 12 to inform the processor 102 that the orthopaedic healthcare provider 60 desires to monitor implant sensor data and/or update the programming of the orthopaedic prosthesis 12. As such, the orthopaedic prosthesis 12 may use any one or more of a number of methods to determine which one or more functions to perform.

If the processor 102 determines that the orthopaedic healthcare provider desires to monitor implant sensor data in step 408, the algorithm 400 advances to process step 412. In process step 412, the processor 102 is configured to transmit the current implant sensor data received from the implant sensor(s) 104 to the controller 14. To do so, the processor 102 is configured to control the cellular transmitter/transceiver 106 to transmit the implant sensor data over the cellular network 18. The implant sensor data may be transmitted in any suitable form. For example, the implant sensor data may be transmitted in compressed or non-compressed form to the controller 14.

Subsequently, in process step 416, the processor 102 determines if any stored implant sensor data should be transmitted to the controller 14. To do so, the processor 102 may be programmed or otherwise configured to transmit or not transmit the stored implant sensor data. Additionally or alternatively, the processor 102 may be configured to access or otherwise retrieve data from the memory device 112 and determine if the stored implant sensor data should be transmitted based on such data (e.g., based on the value of the retrieved data). In this way, the orthopaedic prosthesis 12 may be programmed to transmit stored data or not to transmit stored data depending on the particular application and/or implementation of the system 10 and/or the orthopaedic prosthesis 12.

If the processor 102 determines that any stored implant sensor data should not be transmitted in process step 416, the algorithm 400 loops back to process step 402 wherein the electronic circuitry 100 of the orthopaedic prosthesis 12 waits for the initiation of a new cellular communication from the controller 14. If, however, the processor 102 determines that the implant sensor data stored in the memory device 112 should also be transmitted, the algorithm 400 advances to process step 418. In process step 418, the implant sensor data stored in the memory device 112 is retrieved. The retrieved implant sensor data is subsequently transmitted to the controller 14 in process step 420. To do so, the processor 102 is configured to control the cellular transmitter/transceiver 106 to transmit the retrieved implant sensor data over the cellular network 18. Again, the implant sensor data retrieved from the memory device 112 may be transmitted to the controller 14 in any suitable form including, for example, compressed or non-compressed form. Once the retrieved implant sensor data has been transmitted to the controller 14 in process step 420, the algorithm 400 loops back to process step 402 wherein the electronic circuitry 100 of the orthopaedic prosthesis 12 waits for the initiation of a new cellular communication from the controller 14.

Referring back to process step 410, if the processor 410 determines that orthopaedic healthcare provider desires to update the programming of the electronic circuitry 100, the algorithm 400 advances to process step 422. In process step 422, processor 102 receives programming data from the controller 14 over the cellular network 18 using the cellular transmitter/transceiver 106. Subsequently, in process step 424, the processor 102 is configured to update one or more programs or programming data used by the electronic circuitry 100 using the received programming data depending on, for example, the type of programming data received. For example, in embodiments wherein the programming data is embodied as software/firmware code, the processor 102 may be configured to store the programming data in the memory device 112 and subsequently begin executing the software/firmware code.

In such embodiments, the electronic circuitry 100 may require a "reboot" or otherwise re-initialization to begin executing the new programming code. In other embodiments wherein the programming data is embodied as variable data, the processor 102 may be configured to store the programming data in the memory device 112 such that the programming data overwrites existing data stored therein. In this way, the programming data may alter, change, or update old variable data used by the software and/or firmware executed by the electronic circuitry 100. For example, a data variable indicating if the processor 102 should transmit stored implant sensor data may be stored in the memory device 112 in a known memory location. In such embodiments, the processor 102 is configured to analyze the stored data variable to determine whether to transmit stored implant data. As such, the programming of the orthopaedic prosthesis 12 may be altered, changed, or updated by transmitting a new data value to replace the data variable stored in the memory device 112. Regardless, once the processor 102 has updated the programming of the orthopaedic device 12 with the programming data received from the controller 14, the orthopaedic prosthesis 12 transmits a confirmation signal to the call center 30 to confirm that the programming of the orthopedic prosthesis 12 is complete in process step 426. Subsequently, the algorithm 400 loops back to process step 402 wherein the electronic circuitry 100 of the orthopaedic prosthesis 12 waits for the initiation of a new cellular communication from the controller 14.

Figure 6:
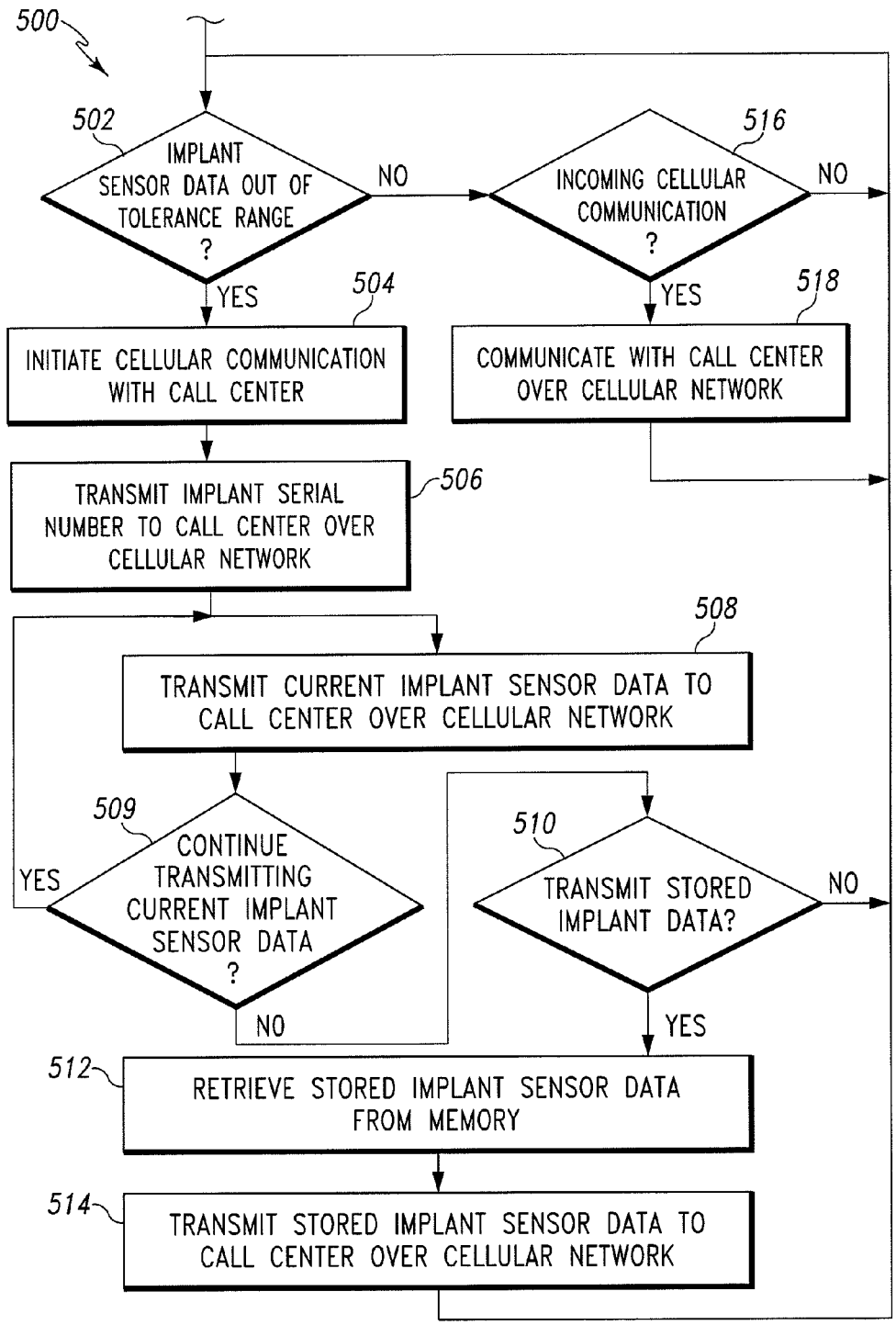
FIG. 6 is a simplified flowchart of another embodiment of an algorithm for communicating with a controller over a cellular network that may be executed by the orthopaedic prosthesis of the system of FIG. 1.
Figure 7:
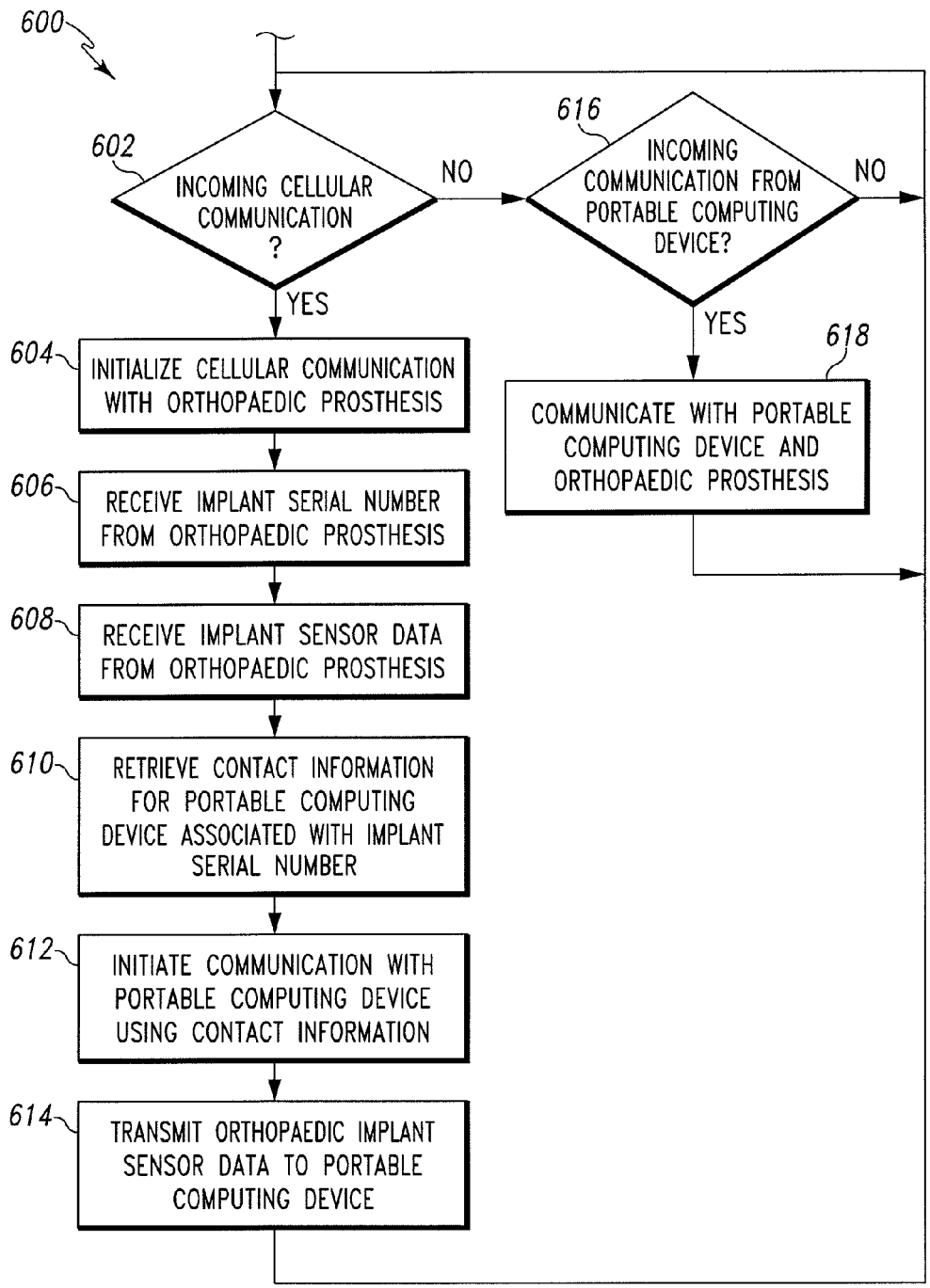
FIG. 7 is a simplified flowchart of another embodiment of an algorithm for communicating with an orthopaedic prosthesis over a cellular network that may be executed by the controller of the system of FIG. 1.
Figure 8:
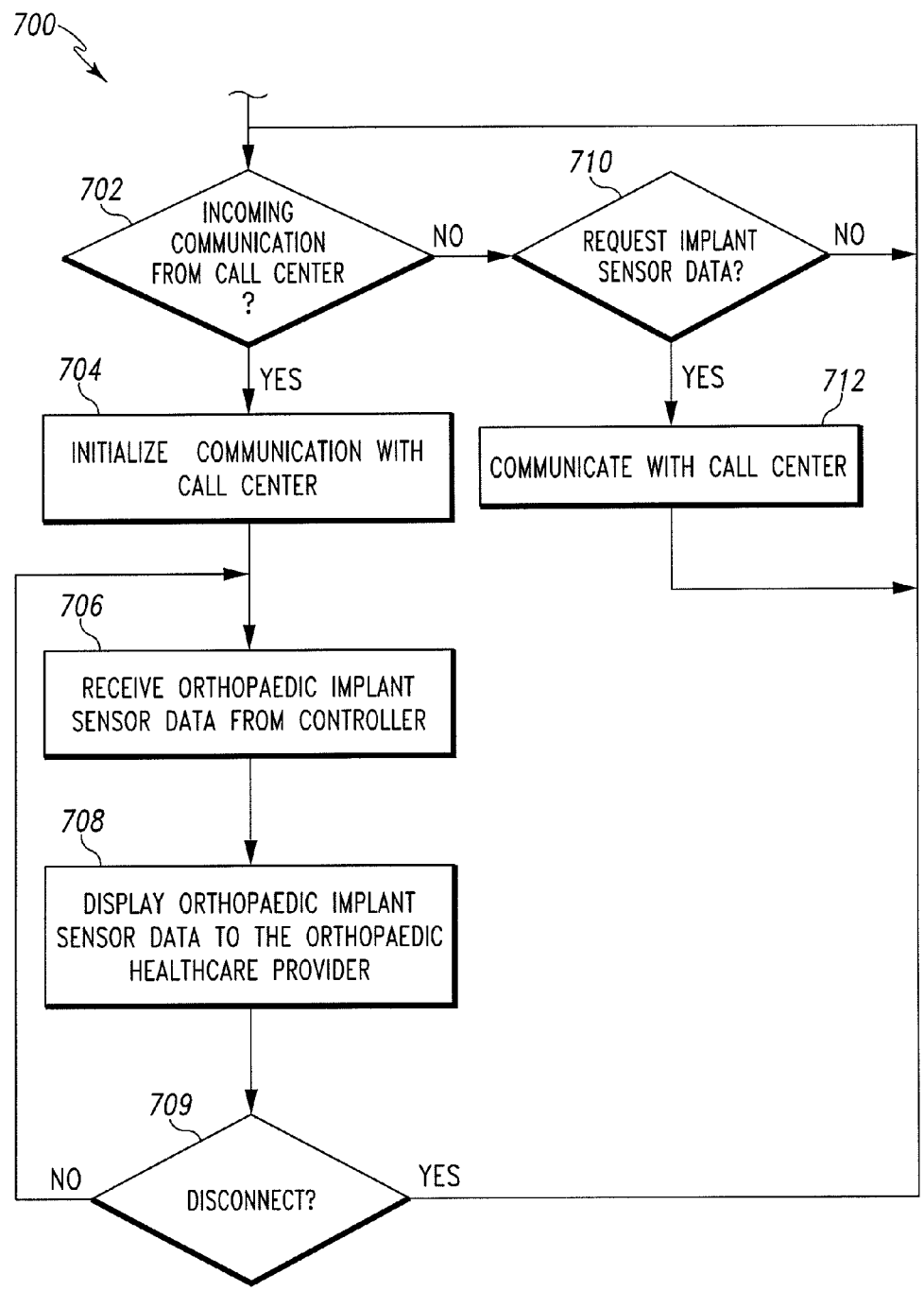
FIG. 8 is a simplified flowchart of another embodiment of an algorithm for communicating with an orthopaedic prosthesis over a cellular network that may be executed by the portable computing device of the system of FIG. 1.

Referring now to FIGS. 6-8, in some embodiments, the orthopaedic prosthesis 12 may be configured to initiate cellular communication with the controller 14 if one or more predetermined conditions occur. In such embodiments, the processor 102 of the orthopaedic prosthesis 12 may be configured to execute an algorithm 500 for communicating with the controller 14 over the cellular network 18 as illustrated in FIG. 6. The algorithm 500 beings with a process step 502 in which the processor 102 determines if the value of the implant sensor data received from any one or more of the implant sensors 104 is out of a tolerance range and/or above or below a predetermined threshold level. For example, if the relevant implant sensor 104 is a pressure sensor configured to generate pressure data, the processor 102 may be configured to determine if the pressure data is above some predetermined maximum allowable pressure value and/or below some predetermined minimum allowable pressure value. To do so, the processor 102 may compare the pressure data received from the implant sensor 104 to a value or values stored in the memory device 112. In such embodiments, the value or values stored in the memory device 112 form a portion of the programming data of the orthopaedic device 12 and, as such, may be changed, altered, or otherwise updated as discussed in detail above in regard to FIGS. 3-5.

If the processor 102 determines that the implant sensor data received from the implant sensor(s) 104 is out of the predetermined tolerance range and/or above or below a predetermined threshold value in process step 502, the algorithm 500 advances to process step 504. In process step 504, the orthopaedic prosthesis 12 initiates cellular communication with the controller 14. To do so, the orthopaedic prosthesis 12 is configured to establish a cellular connection with the controller 14 via use of the cellular transmitter/transceiver 106. For example, the orthopaedic prosthesis 12 may transmit the appropriate data to the cellular network 18 to facilitate the cellular connection. In addition, the orthopaedic prosthesis 12 and the controller 14 may perform any number of initialization steps, "handshaking" steps, or the like to initialize or otherwise establish the cellular communication therebetween.

Once the orthopaedic prosthesis 12 has initiated cellular communication with the controller 14, the orthopaedic prosthesis 12 is configured to transmit the implant serial number associated with the orthopaedic prosthesis 12 in process step 506. To do so, the processor 102 may be configured to retrieve the implant serial number from the memory device 112 and transmit the implant serial number over the cellular network 18 via the communication links 20, 22. Subsequently, in process step 508, the processor 102 is configured to transmit the implant sensor data received from the implant sensor(s) 104 to the controller 14. To do so, the processor 102 is configured to control the cellular transmitter/transceiver 106 to transmit the implant sensor data over the cellular network 18. As discussed above, the implant sensor data may be transmitted in any suitable form. For example, the implant sensor data may be transmitted in compressed or non-compressed form to the controller 14. Subsequently, in process step 509, the processor 102 determines if the orthopaedic prosthesis 12 should continue to send current implant data to the controller 14. If so, the algorithm 500 loops back process step 508 in which the current implant sensor data is transmitted to the controller 14 as described above. In this way, the processor 102 may transmit a stream of current implant data to the controller 14. The orthopaedic prosthesis 12 may be instructed to continue sending the current implant data by a signal received from the controller 14, based on a predetermined transmission time, or a programmable flag or data value. If the processor 102 determines that the orthopaedic prosthesis 12 should continue sending the orthopaedic implant sensor data in process step 509, the algorithm 500 advances to process step 510.

In process step 510, the processor 102 determines if any stored implant sensor data should be transmitted to the controller 14. To do so, the processor 102 may be programmed or otherwise configured to transmit or not transmit the stored implant sensor data. Additionally or alternatively, the processor 102 may be configured to access or otherwise retrieve data from the memory device 112 and determine if the stored implant sensor data should be transmitted based on such data (e.g., based on the value of the retrieved data).

If the processor 102 determines that any stored implant sensor data should not be transmitted in process step 510, the algorithm 500 loops back to process step 502 wherein the processor 102 of the orthopaedic prosthesis 12 determines if the implant sensor data received from the implant sensor(s) 104 is within the predetermined tolerance range. If, however, the processor 102 determines that the implant sensor data stored in the memory device 112 should also be transmitted, the algorithm 500 advances to process step 512. In process step 512, the processor 102 retrieves the implant sensor data from the memory device 112. The retrieved implant sensor data is subsequently transmitted to the controller 14 in process step 514. To do so, the processor 102 is configured to control the cellular transmitter/transceiver 106 to transmit the retrieved implant sensor data over the cellular network 18. Again, the implant sensor data retrieved from the memory device 112 may be transmitted to the controller 14 in any suitable form including, for example, compressed or non-compressed form. Once the retrieved implant sensor data has been transmitted to the controller 14 in process step 514, the algorithm 500 loops back to process step 502 wherein the processor 102 of the orthopaedic prosthesis 12 determines if the implant sensor data received from the implant sensor(s) 104 are within the predetermined tolerance range.

Referring back to process step 502, if the processor determines that the implant sensor data received from implant sensor(s) 104 is within the predetermined tolerance range, the algorithm 500 advances to process step 516. In process step 516, the processor 102 determines if there is any incoming cellular communication from the controller 104. To do so, the processor 102 may monitor the data output of the cellular transmitter/transceiver 106. If the processor 102 determines that there is no incoming cellular communication, the algorithm 500 loops back to process step 502 wherein the processor 102 of the orthopaedic prosthesis 12 determines if the implant sensor data received from the implant sensor(s) 104 are within the predetermined tolerance range.

However, if the processor 102 determines that there is incoming cellular communication from the controller 14 in process step 516, the algorithm 500 advances to process step 518. In process step 518, the processor is configured to communicate with the controller 14 of the call center 30 over the cellular network 18. In process step 516, the processor may transmit implant sensor data, including stored implant sensor data in some embodiments, to the controller 14 over the cellular network 18 and/or receive programming data from the controller 14 over the cellular network 18. As such, it should be appreciated that the processor may execute an algorithm similar to the algorithm 400 illustrated in and discussed above in regard to FIG. 5 in process step 518. For example, the processor 102 may be configured to receive an implant serial number from controller 14, determine the validity of the implant serial number, transmit current and stored implant sensor data to the controller 14, receive programming data from the controller 14, and/or update the programming of the orthopaedic device 12 using the programming data in process step 518. Once the processor 102 has communicated with the controller 14 in process step 518, the algorithm 500 loops back to process step 502 wherein the processor 102 of the orthopaedic prosthesis 12 determines if the implant sensor data received from the implant sensor(s) 104 is within the predetermined tolerance range.

Referring now to FIG. 7, in embodiments wherein the orthopaedic prosthesis 12 is also configured to initiate cellular communication with the controller 14, the controller 14 may execute an algorithm 600 for communicating with an orthopaedic prosthesis 12 over the cellular network 18. The algorithm 600 beings with a process step 602 in which the controller 14 determines if there is incoming cellular communication from the orthopaedic prosthesis 12. If so, the algorithm 600 advances to process step 604 wherein the controller 14 is configured to initialize cellular communication with the orthopaedic prosthesis 12. To do so, the controller 14 may be configured to perform any number of initialization steps, "handshaking" steps, or the like to initialize or otherwise establish the cellular communication with the orthopaedic prosthesis 12.

Once the controller 14 has initialized cellular communication with the orthopaedic prosthesis 12 in process step 604, the controller 14 is configured to receive an implant serial number from the orthopaedic prosthesis 12 over the cellular network 18 in process step 606. In addition, in process step 608, the controller 14 receives implant sensor data from the orthopaedic prosthesis 12 via the cellular network 18. In some embodiments, the controller 14 may be configured to store the implant serial number and/or the implant sensor data in the memory device 28 and/or the database 32.

Once the controller 14 has received the implant serial number and sensor data, the controller 14 is configured to retrieve contact information associated with the portable computing device 16 based on the received implant serial number in process step 610. The contact information may be embodied as any type of data with which the controller 14 may initiate communication with the portable computing device 16 over the network 24. For example, in one embodiment, the contact information may be embodied as or be based on an internet protocol (IP) address or a cellular telephone or access number of the portable computing device 16. Additionally, in some embodiments, the contact information may be embodied as or include an e-mail address or the like. The controller 14 may retrieve the contact information by, for example, retrieving a "look-up" table from the database 32 that indexes implant serial numbers to associated contact information. The controller 14 may then determine the appropriate contact information based on the received implant serial number.

Once the controller 14 has retrieved the contact information for the appropriate portable computing device 16 from the database 32, the controller 14 initiates network communication with the portable computing device 16 in process step 612. To do so, the controller 14 is configured to establish a network connection with the portable computing device 16 over the network 24 using the contact information. For example, the controller 14 may transmit the appropriate data to the network 24 to facilitate the network connection. In addition, the controller 14 and the portable computing device 16 may perform any number of initialization steps, "handshaking" steps, or the like to initialize or otherwise establish the cellular communication therebetween.

Once the controller 14 has initiated communication with the portable computing device 16, the controller 14 is configured to transmit the received implant sensor data to the portable computing device 16 in process step 614. To do so, the controller 14 transmits the received implant sensor data over the network 24 via the communication links 36, 38. Once the controller 14 has transmitted the implant sensor data to the portable computing device 16, the algorithm 600 loops back to the process step 602 wherein the controller 14 is configured to determine if there is any new cellular communication incoming from the orthopaedic prosthesis 12.

Referring back to process step 602, if the controller 14 determines that there is no incoming cellular communication from the orthopaedic prosthesis 12, the algorithm 600 advances to process step 616. In process step 616, the controller 14 determines if there is any incoming communication from the portable computing device 16. If the controller 14 determines that there is no incoming communication, the algorithm 600 loops back to the process step 602 wherein the controller 14 is configured to determine if there is any new cellular communication incoming from the orthopaedic prosthesis 12.

However, if the controller 14 determines that there is incoming communication from the portable computing device 16 in process step 616, the algorithm 600 advances to process step 618. In process step 618, the controller 14 is configured to communicate with the portable computing device 16 over the network 24 and/or the orthopaedic prosthesis 12 over the cellular network 24. In process step 618, the controller 14 receives implant serial numbers and passcodes from the portable computing device 16, receives implant sensor data from the orthopaedic prosthesis 12, and/or transmits implant sensor data to the portable computing device 16 over the network 24. As such, it should be appreciated that the controller 14 may execute a sub-algorithm similar to the algorithm 300 illustrated in and discussed above in regard to FIG. 4 in process step 618. For example, the controller 14 may be configured to receive an implant serial number and passcode from the portable computing device 16, validate the implant serial number and passcode, receive programming data from the portable computing device 16, initiate cellular communication with the orthopaedic prosthesis 12, receive implant sensor data from the orthopaedic prosthesis 12, transmit the implant sensor data to the portable computing device 16, and/or transmit the programming data to the orthopaedic prosthesis 12 in process step 618. Once the controller 14 has communicated with the portable computing device 16 and/or orthopaedic prosthesis 12 in process step 618, the algorithm 600 loops back to process step 602 wherein the controller 14 is configured to determine if there is any new cellular communication incoming from the orthopaedic prosthesis 12.

Referring now to FIG. 8, in embodiments wherein the orthopaedic prosthesis 12 is also configured to initiate cellular communication with the controller 14, the portable computing device 16 may execute an algorithm 700 for monitoring orthopaedic prosthesis data. The algorithm 700 beings with a process step 702 in which the controller 14 determines if there is incoming communication from the controller 14. If so, the algorithm 700 advances to process step 704 wherein the portable computing device 16 is configured to initialize network communication with the controller 14. To do so, the portable computing device 16 may be configured to perform any number of initialization steps, "handshaking" steps, or the like to initialize or otherwise establish the network communication with the controller 14.

Once the communication has been established with the controller 14, the portable computing device 16 receives implant sensor data from the controller 14 in process step 706. As discussed above, the implant sensor data may be current implant sensor data and/or historical implant sensor data generated over a period of time. Subsequently, in process step 708, the received implant sensor data or indicia thereof is displayed to the orthopaedic healthcare provider 60 on a display screen, monitor, or other display device of the portable computing device 16. For example, the implant sensor data may be displayed in numerical form, in a graph, in a chart, or the like. As such, the orthopaedic healthcare provider 60 may be automatically and/or promptly notified if a problem has occurred with the orthopaedic prosthesis 12 as defined by the implant sensor data. The orthopaedic healthcare provider 60 may then subsequently monitor the performance of the orthopaedic prosthesis 12 via the implant sensor data received from the controller 14 and displayed on the portable computing device 16.

In process step 709, the portable computing deice 16 determines if the orthopaedic healthcare provider 60 desires to disconnect from the call center 30 (i.e., stop receiving implant sensor data). If so, the algorithm 700 loops back to process step 702 in which the portable communication device 16 again monitors for any incoming communication from the call center 30. However, if the orthopaedic healthcare provider 60 desires to continue receiving orthopaedic prosthesis data, the algorithm 700 loops back to process step 706 and 708 in which additional current orthopaedic prosthesis data is received and displayed to the orthopedic healthcare provider 60.

Referring back to process step 702, if the portable computing device 16 determines that there is no incoming network communication from the controller 14, the algorithm 700 advances to process step 710. In process step 710, the portable computing device 16 determines if the orthopaedic healthcare provider 60 desires to interact with the orthopaedic prosthesis 12 (e.g., monitor implant sensor data and/or update the programming of the implant 12). If the portable computing device 16 determines that orthopaedic healthcare provider 60 does not desire to interact with the orthopaedic prosthesis 12, the algorithm 700 loops back to the process step 702 wherein the portable computing device 16 is configured to determine if there is any new network communication incoming from the controller 14.

However, if the portable computing device 16 determines that the orthopaedic healthcare provider 60 desires to interact with the orthopaedic prosthesis 12 in process step 710, the algorithm 700 advances to process step 712. In process step 712, the portable computing device 16 is configured to communicate with the controller 14 of the call center 30 over the network 24. In process step 712, the portable computing device 16 is configured to transmit an implant serial number, passcode, and/or programming data to the controller 14, receive implant sensor data from the controller 14, and display the implant sensor data to the orthopaedic healthcare provider 60. As such, it should be appreciated that the portable computing device 16 may execute a sub-algorithm similar to the algorithm 200 illustrated in and discussed above in regard to FIG. 3 in process step 712. For example, the portable computing device 16 may be configured to receive an implant serial number and passcode from the orthopaedic healthcare provider 60, receive programming data from the orthopaedic healthcare provider 60, transmit the implant serial number, the passcode, and the programming data to the controller 14, receive implant sensor data form the controller 14, and display the implant sensor data to the orthopaedic healthcare provider 60 in process step 712. Once the portable computing device 16 has communicated with the controller 14 in process step 712, the algorithm 700 loops back to process step 702 wherein the portable computing device 16 is configured to determine if there is any new network communication incoming from the controller 14.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A medical device comprising:
an implantable orthopaedic prosthesis having secured thereto a circuit, the circuit comprising:
(i) a sensor configured to generate implant sensor data;
(ii) a cellular transceiver configured to receive and transmit data over a cellular network;
(iii) a memory device having stored therein a first implant serial number assigned to the implantable orthopaedic prosthesis; and
(iv) a processor electrically coupled to the sensor, the cellular transceiver, and the memory device, the processor being configured to receive the implant sensor data from the sensor and transmit the implant sensor data over the cellular network using the cellular transceiver in response to the first implant serial number being equal to a second implant serial number received over the cellular network.

2. The medical device of claim 1, wherein:
(i) a cellular transmitter forms a portion of the cellular transceiver configured to receive and transmit data over the cellular network, and
(ii) the processor is configured to transmit the implant sensor data in response to a signal received from a controller over the cellular network via the cellular transceiver.

3. The medical device of claim 1, wherein:
(i) a cellular transmitter forms a portion of the cellular transceiver configured to receive programming data over the cellular network, and
(ii) the processor is configured to update a program of the orthopaedic prosthesis using the programming data.

4. The medical device of claim 1, further comprising a memory device, wherein the processor is configured to:
(i) store the implant sensor data in the memory device,
(ii) retrieve the stored implant sensor data, and
(iii) transmit the retrieved implant sensor data over the cellular network via the cellular transceiver.

5. The medical device of claim 1, wherein the processor is configured to:
(i) compare the implant sensor data to a predetermined threshold value,
(ii) initiate cellular communication with a controller over the cellular network using the cellular transmitter based on the compare step; and
(iii) transmit the implant sensor data to the controller over the cellular network using the cellular transceiver subsequent to the initiate step.

6. The medical device of claim 5, wherein the processor is configured to retrieve implant sensor data from a memory device and transmit the retrieved implant sensor data to the controller over the cellular network using the cellular transceiver subsequent to the initiate step.

7. The medical device of claim 6, wherein the processor is configured to retrieve an implant serial number from the memory device and transmit the implant serial number to the controller over the cellular network using the cellular transceiver subsequent to the initiate step.

8. The medical device of claim 1, wherein the orthopaedic prosthesis comprises a prosthesis selected from the group consisting of: a knee orthopaedic prosthesis, a hip orthopaedic prosthesis, and a shoulder orthopaedic prosthesis.

* * * * *